(12) United States Patent
Leuthardt et al.

(10) Patent No.: US 10,300,251 B2
(45) Date of Patent: May 28, 2019

(54) HIPPOCAMPAL DRUG DELIVERY DEVICES AND METHODS

(71) Applicant: Alcyone Lifesciences, Inc., Lowell, MA (US)

(72) Inventors: Eric Leuthardt, Lowell, MA (US); P J Anand, Lowell, MA (US)

(73) Assignee: Alcyone Lifesciences, Inc., Lowell, MA (US)

( * ) Notice: Subject to any disclaimer, the term of this patent is extended or adjusted under 35 U.S.C. 154(b) by 0 days.

(21) Appl. No.: 15/611,898

(22) Filed: Jun. 2, 2017

(65) Prior Publication Data
US 2017/0348513 A1   Dec. 7, 2017

Related U.S. Application Data

(60) Provisional application No. 62/344,765, filed on Jun. 2, 2016.

(51) Int. Cl.
| | |
|---|---|
| *A61M 25/10* | (2013.01) |
| *A61M 1/00* | (2006.01) |
| *A61M 27/00* | (2006.01) |
| *A61M 5/14* | (2006.01) |
| *A61M 25/01* | (2006.01) |
| *A61M 25/00* | (2006.01) |

(52) U.S. Cl.
CPC .......... *A61M 25/10* (2013.01); *A61M 1/0084* (2013.01); *A61M 27/006* (2013.01); *A61M 5/14* (2013.01); *A61M 25/0108* (2013.01); *A61M 2025/0042* (2013.01); *A61M 2025/1052* (2013.01); *A61M 2205/332* (2013.01); *A61M 2210/0693* (2013.01)

(58) Field of Classification Search
CPC ........ A61M 1/0084; A61M 2025/1052; A61M 2205/332; A61M 2210/0693; A61M 25/0108; A61M 25/10; A61M 5/14
See application file for complete search history.

(56) References Cited

U.S. PATENT DOCUMENTS

| | | | |
|---|---|---|---|
| 4,723,556 A * | 2/1988 | Sussman | A61B 5/031 600/561 |
| 7,014,624 B2 * | 3/2006 | Meythaler | A61M 5/14 600/485 |

* cited by examiner

*Primary Examiner* — Imani N Hayman
(74) *Attorney, Agent, or Firm* — Nutter McClennen & Fish LLP

(57) ABSTRACT

Drug delivery devices and methods are disclosed herein. In some embodiments, a drug can be delivered into a brain ventricle of a subject, where it can diffuse, flow, or otherwise travel across the ependyma and into the hippocampus. The drug can be delivered through a delivery device configured to selectively or transiently obstruct a portion of the ventricle, e.g., the temporal horn or a posterior portion of the temporal horn. The obstruction can define a partitioned volume of the ventricle, limiting or preventing flow of cerebrospinal fluid (CSF) into or out of the partitioned volume. Accordingly, a drug can be delivered into the partitioned volume without being diluted or carried away by CSF, allowing the drug to saturate the ependyma adjacent the hippocampus. The delivery device can allow a high concentration of drug to be achieved and/or maintained within the partitioned volume to enable maximal transependymal penetration to the hippocampus, while reducing the volume of drug needed to achieve a desired therapeutic effect and limiting delivery of the drug to non-targeted areas.

18 Claims, 4 Drawing Sheets

HIPPOCAMPAL DRUG DELIVERY DEVICES AND METHODS

CROSS-REFERENCE TO RELATED APPLICATIONS

The present application claims priority to U.S. Provisional Application No. 62/344,765 filed on Jun. 2, 2016, which is hereby incorporated by reference herein.

FIELD

Devices and methods are disclosed herein for delivering a drug to a subject, e.g., into the temporal horn and/or hippocampus of the subject.

BACKGROUND

There are many instances in which it may be desirable to deliver a drug to a patient. The term "drug" as used herein refers to any functional agent that can be delivered to a human or animal subject, including hormones, stem cells, gene therapies, chemicals, compounds, small and large molecules, dyes, antibodies, viruses, therapeutic agents, etc.

Delivery of the drug can be done in a systemic manner, or can be targeted to a particular location or a particular distribution pattern. Targeted drug delivery can be challenging, however, as there are many instances in which the intended delivery target is not accessible, or not accessible in a minimally-invasive manner. For example, certain areas of the brain, such as the hippocampus, are not easily accessible with a drug delivery device.

In view of these and other challenges, there is a continual need for improved drug delivery devices and methods.

SUMMARY

Drug delivery devices and methods are disclosed herein. In some embodiments, a drug can be delivered into a brain ventricle of a subject, where it can diffuse, flow, or otherwise travel across the ependyma and into the hippocampus. The drug can be delivered through a delivery device configured to selectively or transiently obstruct a portion of the ventricle, e.g., the temporal horn or a posterior portion of the temporal horn. The obstruction can define a partitioned volume of the ventricle, limiting or preventing flow of cerebrospinal fluid (CSF) into or out of the partitioned volume. Accordingly, a drug can be delivered into the partitioned volume without being diluted or carried away by CSF, allowing the drug to saturate the ependyma adjacent the hippocampus. The delivery device can allow a high concentration of drug to be achieved and/or maintained within the partitioned volume to enable maximal transependymal penetration to the hippocampus, while reducing the volume of drug needed to achieve a desired therapeutic effect and limiting delivery of the drug to non-targeted areas.

In some embodiments, a drug delivery method can include inserting a delivery device into a temporal horn of a patient; with the delivery device, blocking the flow of CSF to or from at least a portion of the temporal horn of the patient, thereby defining a partitioned volume; and delivering a drug through a fluid port of the delivery device into the partitioned volume.

The delivery device can include a ventricular catheter. Said blocking can include expanding an expandable component of the delivery device within the temporal horn. Said blocking can include positioning a non-expandable portion of the delivery device within the temporal horn. Said blocking can include deploying a deployable component of the delivery device within the temporal horn. Said blocking can include inflating a balloon portion of the delivery device. The drug can be delivered through a drug delivery lumen of the delivery device and the balloon can be inflated with fluid delivered through an inflation lumen of the delivery device. The drug can be delivered through a drug delivery lumen of the delivery device and the balloon can be inflated through the drug delivery lumen. Inflating the balloon can cause the balloon to contact and form a fluid seal with a ventricular wall of the temporal horn. The balloon can form a negative of the posterior portion of the temporal horn. Inflating the balloon can occlude a posterior portion of the temporal horn. The method can include withdrawing fluid from the partitioned volume. The method can include analyzing the withdrawn fluid to determine a quantity of drug being taken up by the patient. The method can include measuring a force exerted on the ventricle wall by the delivery device. The method can include unblocking the flow of CSF when the measured force exceeds a predetermined threshold. Delivering the drug can cause the drug to diffuse across an ependyma of the patient and into a hippocampus of the patient.

In some embodiments, a drug delivery method can include inserting a catheter into the temporal horn of a patient; inflating a balloon portion of the catheter to block the flow of CSF to or from the temporal horn of the patient; and delivering a drug through a fluid port of the catheter into the blocked temporal horn of the patient.

DETAILED DESCRIPTION

Drug delivery devices and methods are disclosed herein. In some embodiments, a drug can be delivered into a brain ventricle of a subject, where it can diffuse, flow, or otherwise travel across the ependyma and into the hippocampus. The drug can be delivered through a delivery device configured to selectively or transiently obstruct a portion of the ventricle, e.g., the temporal horn or a posterior portion of the temporal horn. The obstruction can define a partitioned volume of the ventricle, limiting or preventing flow of cerebrospinal fluid (CSF) into or out of the partitioned volume. Accordingly, a drug can be delivered into the partitioned volume without being diluted or carried away by CSF, allowing the drug to saturate the ependyma adjacent the hippocampus. The delivery device can allow a high concentration of drug to be achieved and/or maintained within the partitioned volume to enable maximal transependymal penetration to the hippocampus, while reducing the volume of drug needed to achieve a desired therapeutic effect and limiting delivery of the drug to non-targeted areas.

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments. The features illustrated or described in connection with one exemplary embodiment may be combined with the features of other embodiments.

Figure 1:
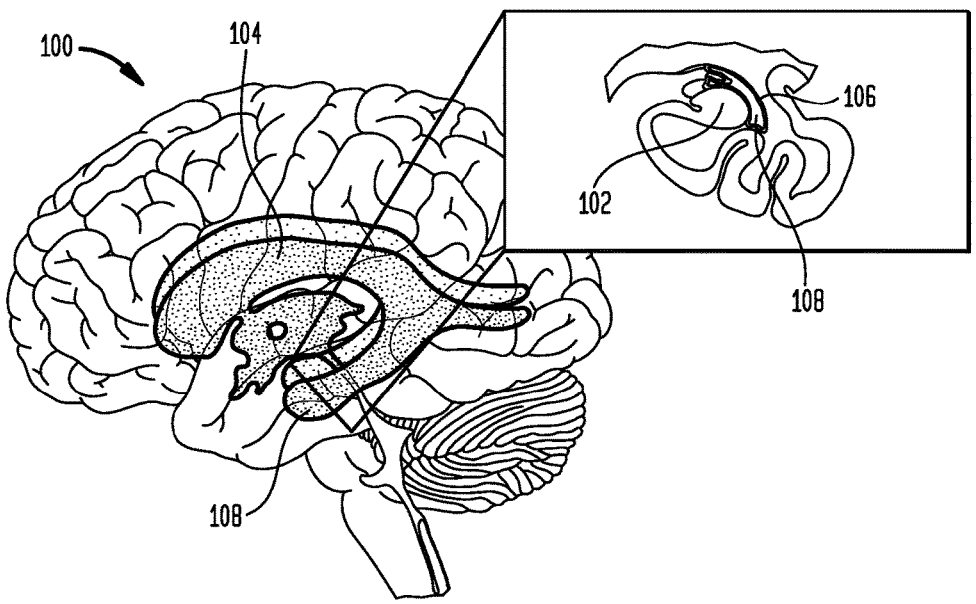
FIG. 1 is a diagram of the human brain with a detail inset showing the hippocampus.

FIG. 1 illustrates a human brain 100, including the hippocampus 102 and surrounding anatomy. As shown, the hippocampus 102 is disposed immediately adjacent to the lateral ventricle 104 and is separated from the lateral ventricle by the ependyma 106—a thin epithelial membrane lining the ventricular system. Generally speaking, the temporal horn 108 (which may also be referred to as the inferior horn) of the lateral ventricle 104 is the portion of the ventricle most proximate to the hippocampus 102.

Figure 2A:
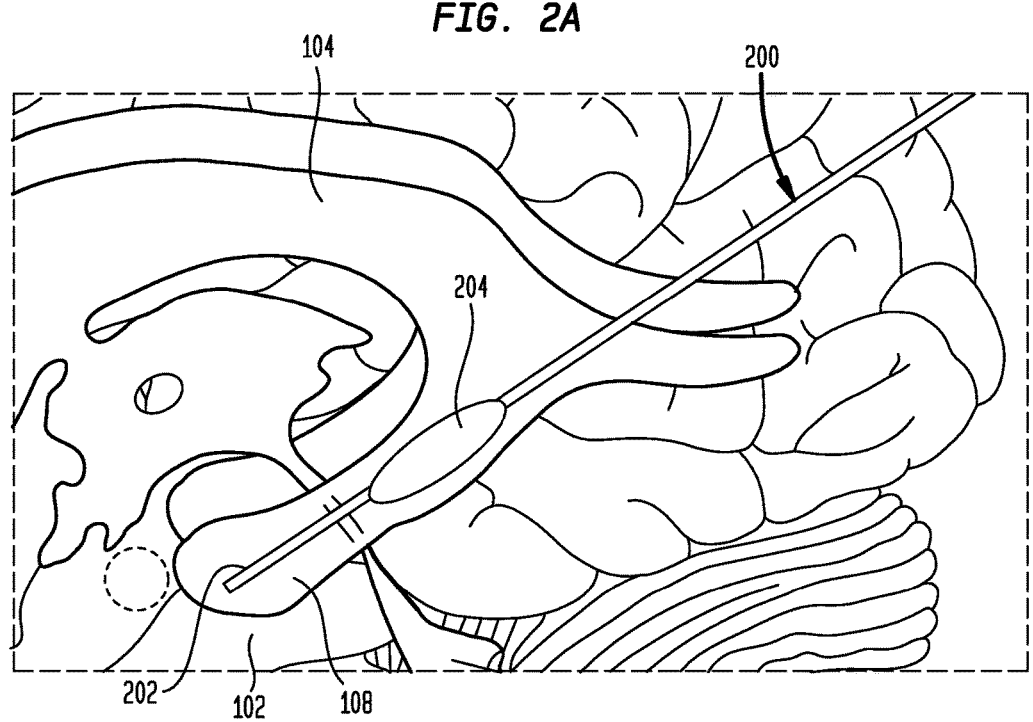
FIG. 2A illustrates a delivery device inserted into a temporal horn of a patient, with an expandable portion of the delivery device in a non-expanded state.
Figure 2B:
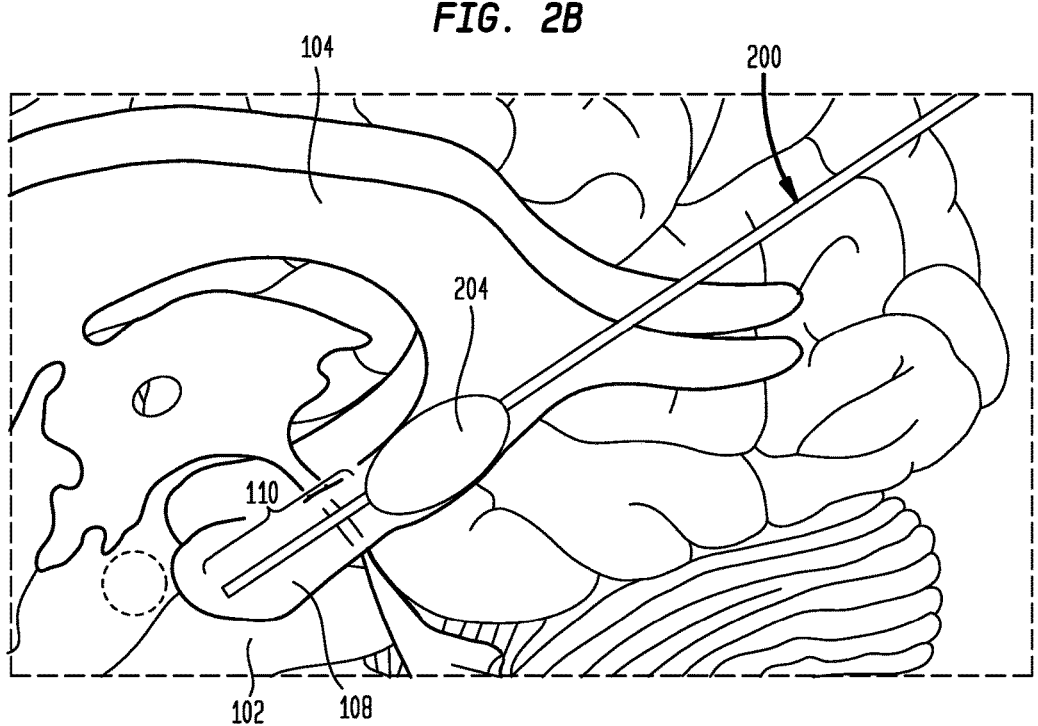
FIG. 2B illustrates a delivery device inserted into a temporal horn of a patient, with an expandable portion of the delivery device in an expanded state.
Figure 2C:
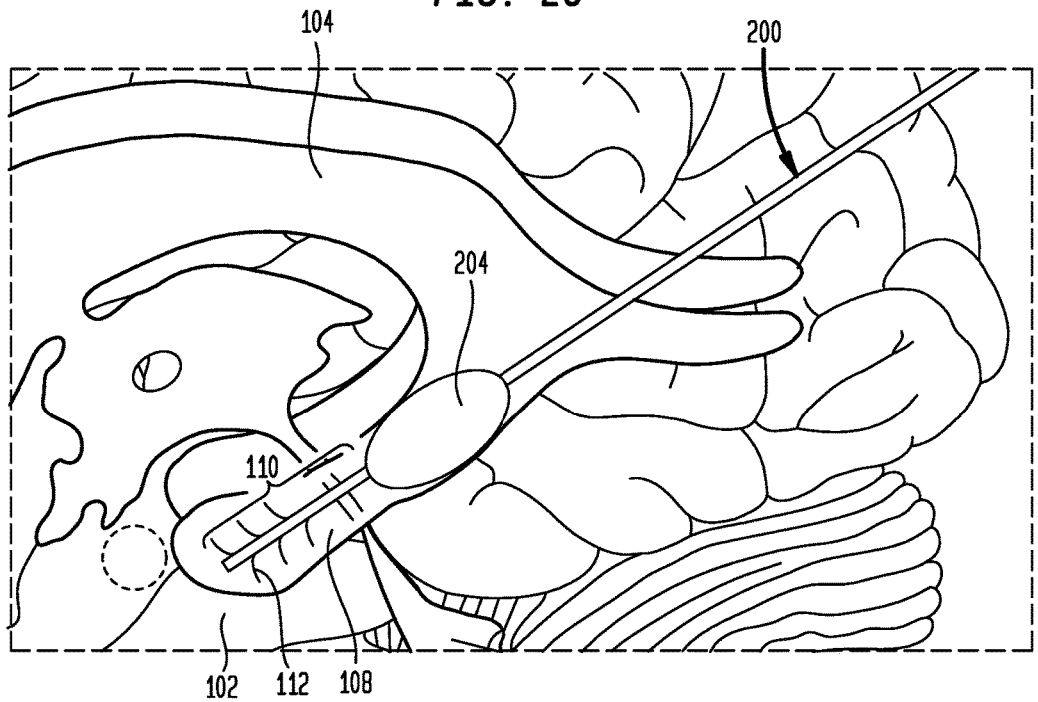
FIG. 2C illustrates a delivery device inserted into a temporal horn of a patient, with a drug being delivered through the device while an expandable portion of the device is in an expanded state.

FIGS. 2A-2C schematically illustrate an exemplary method of hippocampal drug delivery. As shown in FIG. 2A, a drug delivery device 200 can be inserted into the lateral ventricle 104 of a subject. While a catheter with an inflatable balloon is shown, it will be appreciated that any of a variety of delivery devices can be used. The delivery device 200 can be introduced into the ventricle 104 using known techniques, including minimally-invasive ventricular access methods using a surgical navigation system. The delivery device 200 can be positioned such that a fluid outlet port 202 through which a drug can be infused is positioned within the temporal horn 108 of the ventricle 104, e.g., in an anterior portion of the temporal horn adjacent to the hippocampus 102. A blocking portion of the delivery device 200, e.g., an inflatable balloon 204 as shown, can be placed in an unblocked configuration, e.g., a configuration in which the balloon is deflated. In the unblocked configuration, flow of CSF around the delivery device 200 is permitted, e.g., such that CSF can flow into and out of the anterior portion of the temporal horn 108.

As shown in FIG. 2B, the blocking portion of the delivery device 200 can be placed in a blocked configuration to partially or completely obstruct at least a portion of the ventricle 104, thereby defining a partitioned volume 110 distal to the blocking portion. For example, in the case of an inflatable balloon 204, the balloon can be inflated to expand an exterior dimension of the balloon to obstruct the flow of CSF into or out of the partitioned volume 110.

In the illustrated embodiment, the delivery device 200 completely blocks the temporal horn 108, placing the partitioned volume 110 in complete fluid isolation from the rest of the ventricle 104. For example, the delivery device 200 can contact the ventricle wall forming a fluid-tight seal with the ventricle wall. In some embodiments, the delivery device 200 may only partially block the temporal horn 108, such that a small amount of CSF may still flow into or out of the partitioned volume 110. The delivery device 200 can block at least 50% of the cross-sectional area of the posterior temporal horn 108. The delivery device 200 can block at least 75% of the cross-sectional area of the posterior temporal horn 108. The delivery device 200 can block at least 95% of the cross-sectional area of the posterior temporal horn 108.

As shown in FIG. 2C, a drug 112 can be delivered through delivery device 200 and into the partitioned volume 110. The drug 112 can be delivered while the blocking member 204 is in the blocked configuration, such that the blocking member prevents the drug from flowing out of the partitioned volume 110. The obstruction provided by the blocking member 204 can allow for increased concentration of drug 112 in the partitioned volume 110 to enable maximal transependymal penetration to the hippocampus 102.

In the above example, the delivery device includes discrete blocked and unblocked configurations and can be selectively switched between such configurations. In other arrangements, the delivery device can include only a blocked configuration, such that the delivery device automatically occludes the temporal horn when inserted therein and maintains said occlusion as long as the delivery device remains inserted into the temporal horn.

Figure 3A:
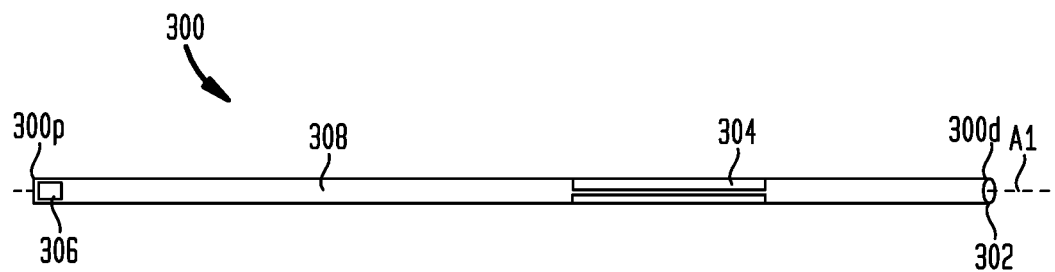
FIG. 3A is a sectional side view of a delivery device, shown in a non-expanded state.
Figure 3B:
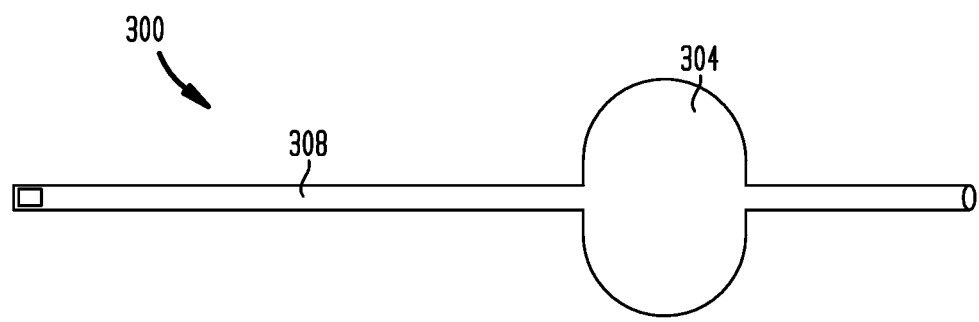
FIG. 3B is a sectional side view of the delivery device of FIG. 3A, shown in an expanded state.

FIGS. 3A-3B illustrate an exemplary delivery device 300 that can be used in the method described above. The illustrated delivery device 300 is a catheter having a proximal end 300p, a distal end 300d, and a central longitudinal axis A1. The catheter 300 can include one or more fluid inlet ports 306, one or more fluid outlet ports 302, and one or more internal fluid lumens 308 for conveying fluid through the catheter between the inlet ports and the outlet ports. The catheter 300 can include a blocking member 304, such as an expandable member, an inflatable balloon, and the like. As shown in FIG. 3A, the catheter 300 can be placed in an unblocked or non-expanded configuration in which the balloon 304 is deflated and the balloon has a reduced exterior dimension. The balloon 304, in the deflated state, can be disposed entirely within the outside diameter of the catheter body, or can protrude only slightly from the catheter body. As shown in FIG. 3B, the catheter 300 can also be placed in a blocked or expanded configuration in which the balloon 304 is inflated or expanded such that the balloon has an enlarged exterior dimension. An interior of the balloon 304 can be in fluid communication with one or more fluid lumens 308 of the catheter. Fluid can be supplied to the balloon 304 via the fluid lumen 308 to inflate the balloon, and can be removed from the balloon via the fluid limen to deflate the balloon.

In use, the distal end 300d of the device 300 can be positioned within an anatomical cavity of a patient, e.g., the temporal horn. The proximal end 300p can remain outside of the patient or can be implanted within the patient. A pump, syringe, reservoir, or other fluid source can be coupled to the proximal end of the catheter to supply fluid thereto and/or to extract fluid therefrom. The fluid source can be extracorporeal or can be partially or completely implanted in the patient. In some embodiments, the delivery device can be fully implanted in the patient for a period of days, weeks, months, etc., e.g., for chronic drug delivery, and can be accessible via a transcutaneous fluid port. The fluid supplied to the catheter can be or can include a drug. The fluid supplied to the catheter can be or can include a buffer, artificial CSF, CSF previously extracted from the patient, saline, etc. The fluid can be used to transport a drug into the patient. The fluid can be used to inflate or expand the blocking member. The fluid can be used to both transport a drug into the patient and to inflate or expand the blocking member.

In FIGS. 3A-3B, the balloon 304 is inflated or deflated through the same lumen 308 as is used for infusing the drug. Accordingly, the balloon 304 can automatically inflate upon delivery of the drug through the catheter 300.

Figure 4:
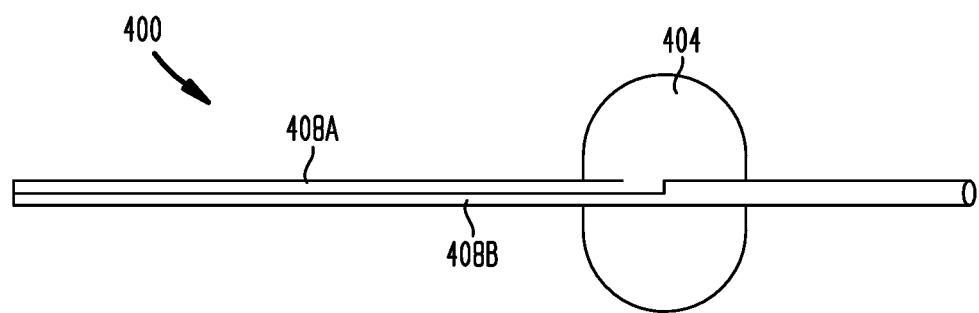
FIG. 4 is a sectional side view of a delivery device with an inflation lumen and a delivery lumen.

In other arrangements, as shown for example in FIG. 4, a catheter 400 can include a dedicated inflation lumen 408A, separate from the drug delivery lumen 408B. This can allow the balloon 404 to be selectively inflated or deflated independently of fluid infusion through the drug delivery lumen 408B.

Figure 5:
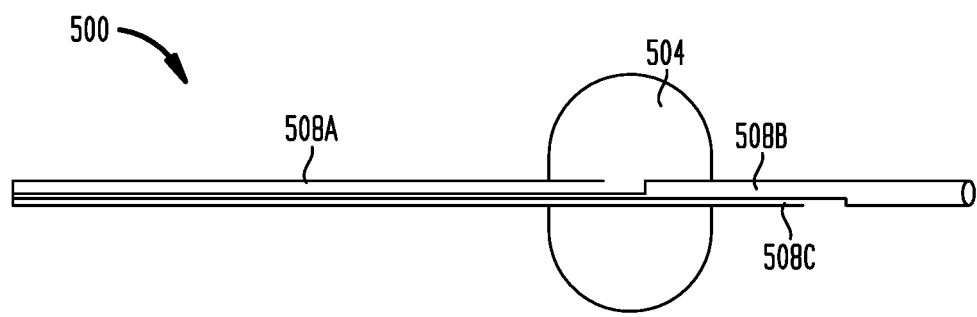
FIG. 5 is a sectional side view of a delivery device with an inflation lumen, a delivery lumen, and an aspiration lumen.

In some embodiments, as shown in FIG. 5, a catheter 500 can include a balloon 504, an inflation lumen 508A used for inflating or deflating the balloon 504, and multiple drug delivery lumens 508B, 508C. This can allow simultaneous infusion of two different drugs. This can allow for a drug to be simultaneously infused through one lumen and withdrawn through another lumen. By establishing inward and outward flow of drug through the catheter, the drug can be continuously circulated through the partitioned volume 110 to maintain a maximum or optimal drug concentration within the partitioned volume. Circulating the drug through the partitioned volume 110 can allow a desired concentration to be maintained within the partitioned volume while also maintaining a constant or substantially constant pressure within the partitioned volume. In some embodiments, fluid being extracted from the partitioned volume 110 can be analyzed to determine the concentration of drug in the aspirated fluid, e.g., to determine how much drug is being taken up (e.g., absorbed, diffused, etc.) into the subject.

Figure 6:
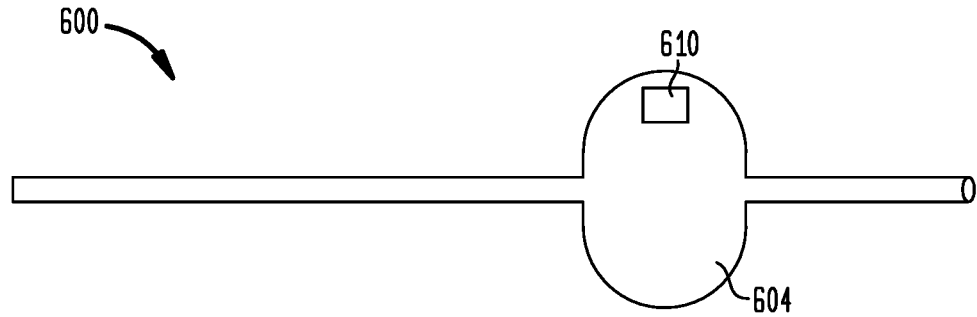
FIG. 6 is a sectional side view of a delivery device with a sensor.

In any of the devices disclosed herein, the balloon can be formed from an elastic material or a non-elastic material. The balloon can be made highly pliable such that the balloon conforms to the ventricular surface during inflation, rather than pushing or deforming the soft ventricle anatomy or the hippocampus, which may be prone to injury if pushed or deformed. In some embodiments, as shown in FIG. 6, a catheter 600 can include a balloon 604 with a sensor 610 for measuring force or pressure applied to the exterior of the balloon. The sensor output can be interpreted to determine whether the balloon is exerting safe amounts of pressure or force onto the surrounding anatomy. The sensor can be operatively coupled to a controller or processor which can generate an alert when the force or pressure applied on the surrounding anatomy exceeds a predetermined threshold, e.g., greater than about 25 cm of water. The controller or processor can be configured to automatically cease inflation of the balloon and/or automatically deflate the balloon when the detected force or pressure exceeds the threshold.

Figure 7:
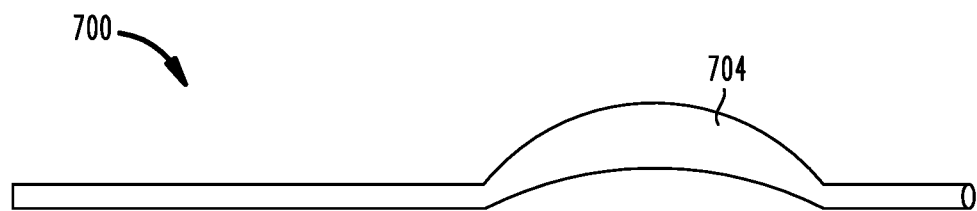
FIG. 7 is a sectional side view of a delivery device with an expandable portion having a banana or kidney shape.

The balloon can have any of a variety of shapes. For example, the balloon can be spherical or substantially spherical. Alternatively, as shown in FIG. 7, a catheter 700 can include a balloon 704 having a banana or kidney shape. The balloon can have a shape that is a negative of at least a portion of the temporal horn or that closely approximates the shape of the temporal horn. The catheter can be provided as part of a kit having a plurality of different balloon shapes and/or balloon sizes. This can allow a user to select the balloon shape and/or size most appropriate for a particular patient. The catheter can include a custom-fabricated balloon sized and shaped to match a specific patient. For example, a patient image (e.g., MRI, CT, PET, X-ray, or the like) can be captured and the size and shape of the region to be occluded can be determined from the captured image. A balloon having an inflated geometry that matches or substantially matches the determined size and shape can be fabricated for use with the patient.

While an inflatable member or balloon is described above, it will be appreciated that the delivery device can include any of a variety of features for occluding the temporal horn. Such features can be included in addition to or in lieu of a balloon. In some embodiments, the main body of the catheter itself can be used to block the temporal horn. In some embodiments, the catheter can include a resilient sheath, wing, expandable component, or other member configured to be deployed within the temporal horn to occlude the temporal horn. The deployable member can be configured to deploy automatically, or can be deployed in response to a stimulus such as temperature, pressure, pH, an electrical signal, an ultrasound signal, and so forth.

In use, the catheter can be inserted into the temporal horn of a patient with the balloon deflated. The catheter can be inserted such that a fluid outlet port of the catheter is disposed in the anterior portion of the temporal horn and such that the balloon is aligned with a posterior portion of the temporal horn. The balloon can then be inflated to partially or completely occlude the posterior portion of the temporal horn. With the balloon inflated, a drug can be delivered through the catheter and the fluid outlet port into the partitioned-off anterior portion of the temporal horn. A high concentration of the drug can be maintained in the temporal horn, promoting diffusion of the drug across the ependyma and into the hippocampus.

Drug delivery to the hippocampus or other regions of the brain or central nervous system using the methods and devices disclosed herein can be used to treat any of a variety of diseases or conditions, such as central-nervous-system (CNS) neoplasm, intractable epilepsy, Parkinson's disease, Huntington's disease, stroke, lysosomal storage disease, chronic brain injury, Alzheimer's disease, amyotrophic lateral sclerosis, balance disorders, hearing disorders, tumors, glioblastoma multiforme (GBM), and cavernous malformations.

It should be noted that any ordering of method steps expressed or implied in the description above or in the accompanying drawings is not to be construed as limiting the disclosed methods to performing the steps in that order. Rather, the various steps of each of the methods disclosed herein can be performed in any of a variety of sequences. In addition, as the described methods are merely exemplary embodiments, various other methods that include additional steps or include fewer steps are also within the scope of the present disclosure.

The devices disclosed herein can be constructed from any of a variety of known materials. Exemplary materials include those which are suitable for use in surgical applications, including metals such as stainless steel, titanium, nickel, cobalt-chromium, or alloys and combinations thereof, polymers such as PEEK, ceramics, carbon fiber, silicone, and so forth. The various components of the devices disclosed herein can be rigid or flexible. One or more components or portions of the device can be formed from a radiopaque material to facilitate visualization under fluoroscopy and other imaging techniques, or from a radiolucent material so as not to interfere with visualization of other structures. Exemplary radiolucent materials include carbon fiber and high-strength polymers.

The devices and methods disclosed herein can be used in minimally-invasive surgery and/or open surgery. While the devices and methods disclosed herein are generally described in the context of drug delivery to the hippocampus, it will be appreciated that the methods and devices disclosed herein can be used in any type of fluid delivery to any anatomical target in a human or animal subject, in non-living objects, and so forth.

Although specific embodiments are described above, it should be understood that numerous changes may be made within the spirit and scope of the concepts described.

The invention claimed is:

1. A drug delivery method, comprising:
   inserting a delivery device into a temporal horn of a patient, such that a fluid port of the delivery device is disposed in a portion of the temporal horn;
   blocking the flow of cerebrospinal fluid (CSF) to or from at least the portion of the temporal horn of the patient in which the fluid port of the delivery device is disposed by expanding an expandable component of the delivery device, thereby defining a partitioned volume; and
   delivering a drug through the fluid port of the delivery device into the partitioned volume.

2. The method of claim 1, wherein the delivery device comprises a ventricular catheter.

3. The method of claim 1, wherein said blocking comprises positioning a non-expandable portion of the delivery device within the temporal horn.

4. The method of claim 1, wherein said blocking comprises deploying a deployable component of the delivery device within the temporal horn.

5. The method of claim 1, wherein expanding the expandable component of the delivery device comprises inflating a balloon portion of the delivery device.

6. The method of claim 5, wherein the drug is delivered through a drug delivery lumen of the delivery device and the balloon portion of the delivery device is inflated with fluid delivered through an inflation lumen of the delivery device.

7. The method of claim 5, wherein the drug is delivered through a drug delivery lumen of the delivery device and the balloon portion of the delivery device is inflated through the drug delivery lumen.

8. The method of claim 5, wherein inflating the balloon portion of the delivery device causes the balloon portion of the delivery device to contact and form a fluid seal with a ventricular wall of the temporal horn.

9. The method of claim 5, wherein the balloon portion of the delivery device forms a negative of a posterior portion of the temporal horn.

10. The method of claim 5, wherein inflating the balloon portion of the delivery device occludes a posterior portion of the temporal horn.

11. The method of claim 1, further comprising withdrawing fluid from the partitioned volume.

12. The method of claim 11, further comprising analyzing the withdrawn fluid to determine a quantity of drug being taken up by the patient.

13. The method of claim 1, further comprising measuring a force exerted on a ventricle wall by the delivery device.

14. The method of claim 13, further comprising unblocking the flow of CSF when the measured force exceeds a predetermined threshold.

15. The method of claim 1, wherein delivering the drug causes the drug to diffuse across an ependyma of the patient and into a hippocampus of the patient.

16. A drug delivery method, comprising:
   inserting a catheter into a temporal horn of a patient, such that a fluid port of the catheter is disposed in a portion of the temporal horn;
   inflating a balloon portion of the catheter to at least partially block the flow of cerebrospinal fluid (CSF) to or from at least the portion of the temporal horn of the patient in which the fluid port is disposed; and
   delivering a drug through the fluid port of the catheter into the blocked portion of the temporal horn of the patient.

17. A drug delivery method, comprising:
   inserting a delivery device into a temporal horn of a patient;
   with the delivery device, blocking the flow of cerebrospinal fluid (CSF) to or from at least a portion of the temporal horn of the patient, thereby defining a partitioned volume, wherein said blocking comprises inflating a balloon portion of the delivery device; and
   delivering a drug through a fluid port of the delivery device into the partitioned volume, wherein the drug is delivered through a drug delivery lumen of the delivery device and the balloon portion of the delivery device is inflated with fluid delivered through an inflation lumen of the delivery device.

18. A drug delivery method, comprising:
   inserting a delivery device into a temporal horn of a patient;
   with the delivery device, blocking the flow of cerebrospinal fluid (CSF) to or from at least a portion of the temporal horn of the patient, thereby defining a partitioned volume;
   delivering a drug through a fluid port of the delivery device into the partitioned volume;
   withdrawing fluid from the partitioned volume; and
   analyzing the withdrawn fluid to determine a quantity of drug being taken up by the patient.

* * * * *